Figure 1:
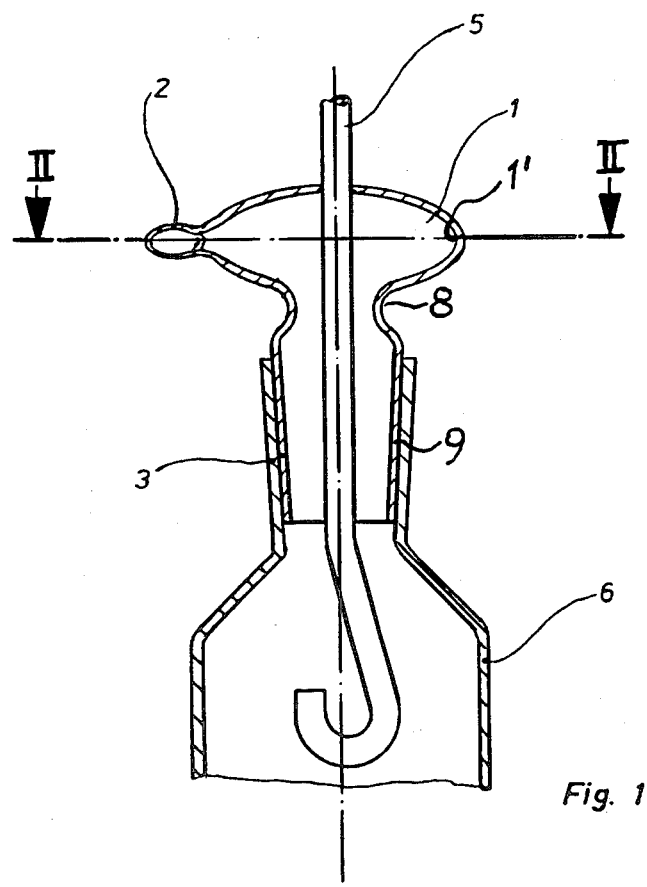

United States Patent [19]

Brüning et al.

[11] 4,228,129
[45] Oct. 14, 1980

[54] CLEANING ATTACHMENT TO CLEAN FLASK-SHAPED RECEIVERS OF CHEMICAL ANALYSIS APPARATUS

[75] Inventors: Rolf Brüning, Bruchköbel; Jürgen Roth, Maintal, both of Fed. Rep. of Germany

[73] Assignee: Heraeus Quarzschmelze GmbH, Hanau, Fed. Rep. of Germany

[21] Appl. No.: 50,317

[22] Filed: Jun. 20, 1979

[30] Foreign Application Priority Data

Jul. 22, 1978 [DE] Fed. Rep. of Germany ....... 2832348

[51] Int. Cl.³ ............................ B01L 3/00; B08B 3/08; B08B 9/08
[52] U.S. Cl. ................................ 422/102; 134/166 R; 422/99; 422/101; 422/103
[58] Field of Search ................. 422/99, 101, 102, 103; 134/22 R, 166 R

[56] References Cited

U.S. PATENT DOCUMENTS

| 2,317,101 | 4/1943 | Lecky | 422/102 X |
| 3,348,827 | 10/1967 | Trefzer | 422/102 X |

FOREIGN PATENT DOCUMENTS 1032000 11/1958 Fed. Rep. of Germany.
1498722 9/1972 Fed. Rep. of Germany.
1098407 1/1968 United Kingdom.

OTHER PUBLICATIONS

Heraeus Quarzschmelze GmbH Brochure Q-E2/111; "Verbrennungsapparatur nach Wickbold Typ 4".
Heraeus-Schott Quarzschmelze GmbH Brochure Q--E1/111; "Verbrennungs Apparaturen nach Dr. Wickbold".

*Primary Examiner*—Barry S. Richman
*Attorney, Agent, or Firm*—Frishauf, Holtz, Goodman & Woodward

[57] ABSTRACT

An essentially circular header is formed with an interior trough to which a supply duct for cleaning fluid, terminating therein tangentially so that cleaning fluid introduced through the supply duct into the trough of the header and flowing thereinto will be subjected to a swirling motion. The header terminates in a neck portion of substantially reduced diameter which has an outer conically converging surface which fits into a conically diverging surface of a flask, receiver, or other chemical apparatus to be cleaned. Preferably, the neck portion is shorter than the receiving end of the mouth portion of the receiver so that a swirling film of liquid will flow downwardly, by gravity, from the receiver through the neck portion and into the still converging mouth portion of the receiver to be cleaned, to then spread out along the inner walls of the receiver, while still swirling, and efficiently clean the receiver element, without requiring disassembly of the receiver element from remaining portions of the chemical analysis apparatus.

10 Claims, 2 Drawing Figures

CLEANING ATTACHMENT TO CLEAN FLASK-SHAPED RECEIVERS OF CHEMICAL ANALYSIS APPARATUS

The present invention relates to chemical analysis apparatus, and more particularly to a cleaning attachment which can be associated with, or combined with, flask-shaped receivers used, for example in various types of chemical analysis processes.

BACKGROUND AND PRIOR ART

Chemical analysis apparatus, particularly of the type using combustion apparatus, such as for example oxy-hydrogen combustion apparatus, are frequently used to determine the presence of organic substances, metals, and the like, within substances which may be in various states, for example gases. The substances are combusted or otherwise treated and then processed and conducted to a distillation receiver or recipient which may, for example, be a flask which also may be subjected to external cooling, or other conditioning.

Apparatus of this type is well known and commercially available, and described, for example, in British Pat. No. 1,098,407; German Pat. No. 1,498,722, and German Pat. No. 1,032,000. It is manufactured by the assignee of the present application and described in literature prospectus materials Q-E1/111 and Q-E2/111. The apparatus described in German Pat. No. 1,498,722 is directed to a continuously operating detonating gas, or oxy-hydrogen gas combustion apparatus to permit rapid serial analysis of substances for organic elementary analysis.

Some substances which are to be determined leave residual traces in the vessels of the analysis apparatus and, specifically, may collect in the distillation receiver or recipient where their presence may lead to erroneous determination of substances subsequently supplied to the analysis apparatus.

THE INVENTION

It is an object to provide a simple and effective cleaning or flushing apparatus for chemical analysis devices, which is separable from the devices and permits cleaning of the devices without disassembling them from the remainder of the analysis system.

Briefly, an attachment is provided which has a header of essentially circular cross section formed with an interior trough. A supply duct extends into the header and terminates upwardly of the trough for supply of a cleaning liquid thereto, the supply duct terminating at the trough in a tangential direction. The header has a converging neck portion positioned downwardly of the trough, formed with an outer surface matching a conically divergent upper mouth of the flask-shaped receiver or other device of the chemical analysis system which is to be cleaned. Usually, the receiver will be of glass and have ground-glass mouth; the conically converging neck portion then, likewise, preferably has a ground-glass outer surface so that the two surfaces match accurately.

The diameter of the header at the trough region is substantially greater than the diameter of the conically converging neck which fits into the mouth of the receiver which is to be cleaned. Application of cleaning fluid to the supply duct, then, will result in effective and intensive wetting of the entire inner surface of the header and cause the cleaning fluid to run down through the converging neck portion, while still swirling and effectively spreading over the entire circumference of the interior surface of the flask-shaped chemical analysis device which is to be cleaned. The interior surface of the flask-shaped receiver which is in contact with the substance to be analyzed thus is cleaned and wetted over its entire interior area. A film of cleaning liquid will uniformly flow along the entire interior surface of the receiver, running down under gravity, but wetting the surface throughout its extent, without leaving off any portions due to surface tension or the like. Cleaning is effectively accomplished and replacement of the receiver within the analysis system due to contamination by substances to be analyzed is no longer necessary.

The cleaning attachment can be easily applied to any receiver within a multiple unit analysis system and can be tightly connected to the receiver itself.

In a preferred form, a metering valve is included in the supply duct, and the neck portion of the cleaning attachment apparatus terminates short of the smallest end of the diverging mouth portion of the receiver with which it is to be used so that a film of cleaning liquid will already form on the mouth portion to then spread out within the receiver itself. The entire header of the cleaning attachment preferably is made of laboratory-type glass, quartz glass, or the like.

Figure 2:
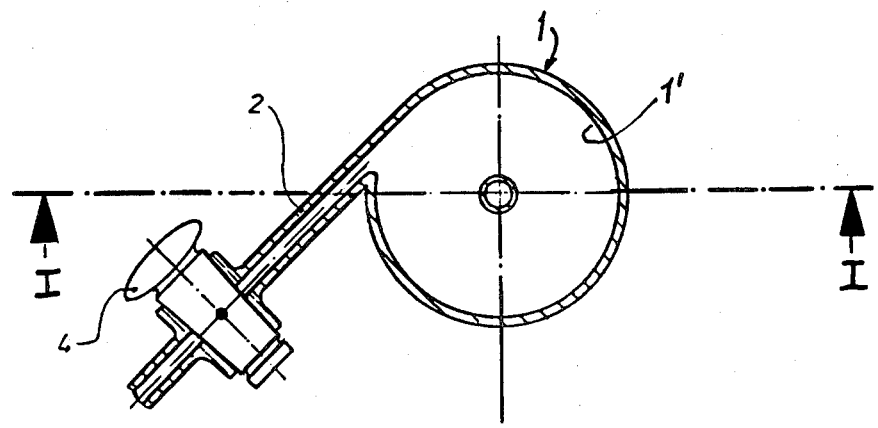

Drawing, illustrating a preferred example:

FIG. 1 is a highly schematic longitudinal cross-sectional view through the cleaning attachment and the top portion of a receiver which is to be cleaned, taken along lines I—I of FIG. 2; and FIG. 2 is a horizontal cross section through the cleaning attachment taken along lines II—II of FIG. 1.

The cleaning attachment is adapted to fit on a flask or other type of receiver in chemical distillation apparatus, typically a distillation recipient. FIG. 1 shows only the upper, or mouth portion of a distillation recipient 6. As customary in chemical apparatus, it is made of glass, such as laboratory-type glass, quartz glass, or the like, and formed with a conically divergent mouth portion which has a ground inner surface, so that a stopper or other element can be accurately fitted therein. The cleaning attachment itself has a header 1 formed with a circumferential trough or groove 1'. A supply duct 2 for cleaning and rinsing liquid terminates tangentially in the trough 1'. The lower portion of the header 1 is formed with a constriction 8 which then merges into a conically converging neck 9. The neck 9 has an outer surface which accurately matches the inner surface of the mouth portion 3 of the receiver 6 and, preferably, also has a ground-glass surface. The ground-glass surface on the neck portion 9 fitting the mouth 3 provides tight engagement of the cleaning attachment with the receiver, and particularly with the upper portion thereof. Preferably, the neck portion 9 is slightly shorter than the mouth portion 3 of the receiver 6, terminating above the ring at which the mouth portion 3 merges with the remainder of the receiver 6, to provide for smooth transition of the inner surface of the neck portion 9 to the receiver 6.

A metering valve 4 (FIG. 2) is preferably included in the duct 2.

A tube 5 is inserted in the header 1, extending beyond the mouth and neck portions of the receiver and the attachment, and into the receiver 6 itself. The tube 5 can be used as a vacuum connection tube to apply suction thereto, but may also be used to introduce gases, liquids, or other mixtures. The cleaning attachment 1, preferably, is also made of glass, such as laboratory-type glass, quartz or the like.

In operation, tangential supply of cleaning and/or rinsing liquid, preferably under pressure, causes a rotating film of fluid to collect in the trough 1' and to run downwardly, uniformly along the inner wall of the cleaning attachment, through the constriction 8, the neck portion 9, and into the mouth portion 3 of the receiver 6. The ground-glass connection between the mouth 3 and the neck 6 is so made that the transition of fluid is preferably smooth and without introducing substantial turbulence. The wall thickness of the neck portion 9, therefore, preferably, is thin, and particularly at the lower portion thereof; terminating a thinned end of the neck portion 9 above the merger line of the mouth portion 3 with the remainder of the receiver 6 further assists in uniformity of dispersion of the cleaning fluid around the entire surface of the walls of the receiver 6. The film, then, can smoothly flow down, while still rotating, without interruption, tears or fissures in a continuing flow of liquid from the trough 1', through the engaging neck and mouth portions 9, 3 into the remainder of the mouth portion of the receiver 6, and then along the inner surface of the side walls of the receiver 6. The differential pressure in the interior of the receiver 6 and of the supply of liquid through duct 2 may be only 100 millibar; even with such a low differential pressure, the liquid introduced in the receiver 6 will have such a high speed that the trough 1' will have a rapidly rotating film of liquid collect therein which is stabilized by centrifugal force. The inlet duct 2 preferably is a capillary tube with an interior diameter of about 1.5 mm.

The end of the communicating tube 5 is preferably so made that the lower end is hook-shaped (FIG. 1), angled, and inclined or otherwise deviating from a straight axial tube, in order to prevent introducing droplets of the liquid in the container 6 upon application of suction to the tube 5.

Various changes and modifications may be made within the scope of the inventive concept.

We claim:

1. In combination with chemical analysis apparatus including a flask-shaped receiver (6) having a conically divergent upper mouth (3),
    a cleaning attachment for removable association with said receiver to clean the receiver without disassociating said receiver from the apparatus,
    said attachment comprising,
    a header (1) which is essentially circular in cross section and formed with an interior trough (1');
    a supply duct (2) extending into the header and terminating in fluid communication with the trough and tangentially with respect thereto;
    and a conically converging neck portion (3) positioned downwardly of the trough and having an outer surface matching the conically divergent upper mouth of the flask-shaped receiver for accurate and tight fit thereinto.

2. A combination according to claim 1, wherein the diameter of the header (1) at the trough (1') is large with respect to the maximum diameter of the converging neck portion (9).

3. A combination according to claim 1, wherein the neck portion (9) of the header (1) is shorter than the mouth portion (3) of the receiver (6), so that the lower end of the neck portion will terminate short of the merger line of the mouth portion (3) of the receiver with the remainder of the receiver (6).

4. A combination according to claim 1, further including a metering valve (4) included in the supply duct (2).

5. A combination according to claim 1, wherein said flask-shaped receiver is constructed of glass and the conically divergent surface is a ground-glass surface,
    wherein the attachment is made of glass, and the outer surface of the conically converging neck portion (9) is ground to form a close, tight ground glass-to-glass fit with the mouth portion (3) of the receiver (6).

6. A combination according to claim 5, wherein the diameter of the header (1) at the trough (1') is large with respect to the maximum diameter of the converging neck portion (9);
    the supply duct comprises a capillary tube of approximately 1.5 mm inner diameter;
    a valve is included in the fluid communication to the supply duct (2);
    the neck portion (9) of the header (1) is shorter than the mouth portion (3) of the receiver (6), so that the lower end of the neck portion will terminate short of the merger line of the mouth portion (3) of the receiver with the remainder of the receiver (6);
    and a communicating tube (5) extends through the header (1) and into the region of the receiver (6) and below the lowest extent of the neck portion.

7. A combination according to claim 1, wherein the supply duct (2) is a capillary tube.

8. A combination according to claim 7, wherein the capillary tube has a diameter in the order of about 1.5 mm.

9. A combination according to claim 1, further including a communicating tube (5) extending through the header (1) and into the region of the receiver (6) and below the lowest extent of the neck portion.

10. A combination according to claim 9, wherein the free end of the tube (5) is angled off from the longitudinal axis of the receiver to prevent introduction of droplets into the tube upon application of suction thereto.

* * * * *